United States Patent [19]

Tubert et al.

[11] Patent Number: 6,137,029
[45] Date of Patent: Oct. 24, 2000

[54] PEPCK-INSULIN GENE CONSTRUCT AND TRANSGENIC MOUSE

[75] Inventors: Fatima Bosch Tubert; Alfons Valera Abril, both of Cerdanyola, Spain

[73] Assignee: Universitat Autonoma De Barcelona, Bellaterra, Spain

[21] Appl. No.: 08/553,576
[22] PCT Filed: Mar. 14, 1994
[86] PCT No.: PCT/ES94/00027
§ 371 Date: Jun. 3, 1996
§ 102(e) Date: Jun. 3, 1996
[87] PCT Pub. No.: WO95/25169
PCT Pub. Date: Sep. 21, 1995

[51] Int. Cl.[7] ............ C12N 15/09; C12N 15/63; C12N 15/00; C12N 5/00
[52] U.S. Cl. .............. 800/18; 800/9; 435/455; 435/456; 435/320.1; 435/325; 514/44
[58] Field of Search ............ 514/3, 44; 536/23.1; 435/240.1, 320.1, 455, 456, 325; 800/18, 9

[56] References Cited

FOREIGN PATENT DOCUMENTS 8810304   12/1988   WIPO.

OTHER PUBLICATIONS

Stewart et al. J. of Mol. Endocrinology 11:335–341 (1993).
McGrane et al. J. of Biol. Chem. 263(23):11443–11451 (1988).
Selden et al. The New England J. of Med. 317(17) 1067–1076 (1987).
Bucchini et al. PNAS 83:2511–2515 (1986).
Chrystal, Science 270: 404–410 (1995).
Cedley, Hum. Gen. Ther. 6:1129–1144 (1995).
Morsy et al JAMA 270(19): 2338–2345 (1993).
Karlsson, Blood 78(10): 2481–2492(1991).
"Identification of a cAMP Regulatory Region in the Gene for Rat Cytosolic Phosphoenolpyruvate Carboxykinase GTP)" A. Wynshaw–Boris, The Journal of Biological Chemistry, vol. 259, No. 19, Issue of Oct. 10, pp. 12161–12169, 1984.
"Characterization of the Phosphoenolpyruvate Carboxykinase (GTP) Promoter–regulatory Region" A. Wynshaw–Boris, et al., The Journal of Biological Chemistry, vol. 261, No. 21, Issue of Jul. 25, pp. 9714–9720.
"Identification of a Sequence in the PEPCK Gene That Mediates a Negative Effect of Insulin on Transcription" R.M. O'Brien, et al., Science, vol. 249, pp. 533–537 (1990).
"Rapid Loss of Translatable Messenger RNA of Phosphoenolpyruvate Carboxykinase During Glucose . . . Liver" S.M. Tilghman, et al., Proc. Nat. Acad. Sci. USA, vol. 71, No. 4, pp. 1304–1308, Apr. 1974.
"Synthesis and Degradation of Phosphoenolpyruvate Carboxylase in Rat Liver and Adipose Tissue" M.F. Hopgood, et al., Biochem. J. (1973) 134, Dec. 29, 1972, pp. 445–453.
"Alterations in Translatable Messenger RNA Coding for Phosphoenolpyruvate Carboxykinase (GTP) . . . Deinduction" D. Kioussis, et al., The Journal of Biological Chemistry, vol. 253, No. 12, Issue of Jun. 25, 1978, pp. 4327–4332.
"Tissue–Specific, Developmental, Hormonal, and Dietary Regulation of Rat Phosphoenolpyruvate Carboxykinase . . . Mice" M.K. Short, et al., Molecular and Cellular Biology, vol. 12, No. 3, Mar. 1992, pp. 1007–1020.
"Differential Regulation of the Rat Phosphoenolpyruvate Carboxykinase Gene Expression in Several Tissues . . . Mice" C.L. Eisenberger, et al., Molecular and Cellular Biology, vol. 12, No. 3, Mar. 1992, pp. 1396–1403.
"Regulated expression of human insulin in the liver of transgenic mice corrects diabetic alterations" A. Valera, et al., The FASEB Journal, vol. 8, NP. 6, Apr. 1, 1994, pp. 440–447.
"Approaches to Diabetes Gene Therapy Using Insulin Gene Driven by P–Enolpyruvate Carboxykinase Promoter," A. Valera et al., Journal of Cellular Biochemistry, Supplement 17E, 1993, Mar. 29 –Apr. 25, 1993, p. 252.
"Regulated Expression of Human Insulin in the Liver of Transgenic Mice Corrects Diabetic Alterations" X, Gregori et al, Journal of Cellular Biochemistry, Supplement 18A, Jan. 4–23, 1994, p. 145.
"Characterization of the Phosphoenolpyruvate Carboxykinase (GTP) Promoter–regulatory Region", Jul. 25, 1986 Jay M Short, et al., The Journal of Biological Chemistry, vol. 261, pp. 9721–9726.

Primary Examiner—Jasemine C. Chambers
Assistant Examiner—Jill D. Martin
Attorney, Agent, or Firm—Steinberg & Raskin, P.C.

[57] ABSTRACT

The chimeric gene is directed by a promoter or fusion of promoters which preferably are regulable and activated by the diabetic process. Preferably, it is obtained by fusion of the human insulin gene to the promoter of PEPCK (P-enolpiruvate carboxiquinasa). Said promoter (fragment –460 bp to +73 bp) is fused to the flank zone 5' of the human insulin gene (–170 bp to +1). The gene of the human insulin contains two coding exons E1 and E2 and two introns A and B. It also relates to an expression vector which allows the expression of insulin in cells which are different from the β-cells of the pancreas, and to a transgenic mouse which expresses said chimeric gene.

13 Claims, 3 Drawing Sheets

PEPCK-INSULIN GENE CONSTRUCT AND TRANSGENIC MOUSE

This 371 application claims the benefit of PCT/ES94/00027, filed Mar. 14, 1994.

The present invention relates firstly to a chimeric gene using the gene or cDNA (complementary DNA) of insulin driven by a promoter or fusion of promoters.

More specifically, it relates to the design of a chimeric gene formed by the fusion of the promoter of P-enolpgruvate carboxyquinase to the structural gene of human insulin, which allows the production of human insulin, physiologically regulated, in a tissue different from the pancreas.

The invention further relates to others objects which are described below.

BACKGROUND OF THE INVENTION

Patients suffering from insulin dependent diabetes mellitus (IDDM) (type I) depend dramatically on the administration of the hormone. The interruption of the insulin administration results first in hyperglycemia and ketoacidosis, then coma and finally death if the hormone is not injected. Therefore, the life and the quality of life of these patients depend completely on the fluctuations of the insulin levels in their blood.

Gene therapy consists in the transfer of genetic material into cells of a patient with the purpose of treating an illness. At present, different approximations of gene therapy are being developed, based on the introduction of genes directly into animals or cells which are then transplanted.

However, the most important goal is not to be able to transplant successfully cells expressing the gene in an animal, but to make it possible for the gene to express in a regulated and physiologic way. The choice of a good promoter which drives the expression of the suitable gene is crucial in order to obtain suitable plasmatic levels of the corresponding protein.

In the case of diabetes, the question is to chose the promoter which drives the expression of the gene in order to obtain suitable insulin plasmatic levels for every condition of the individual. The overexpression of the insulin gene would result in hypoglucemia and a low expression of said gene would not modify the high glucose levels in the diabetic process.

BRIEF DESCRIPTION OF THE DRAWINGS

In order to better understand the disclosure herein, we enclose some drawings concerning examples of embodiments.

In said drawings.

DESCRIPTION OF THE INVENTION

Figure 1:
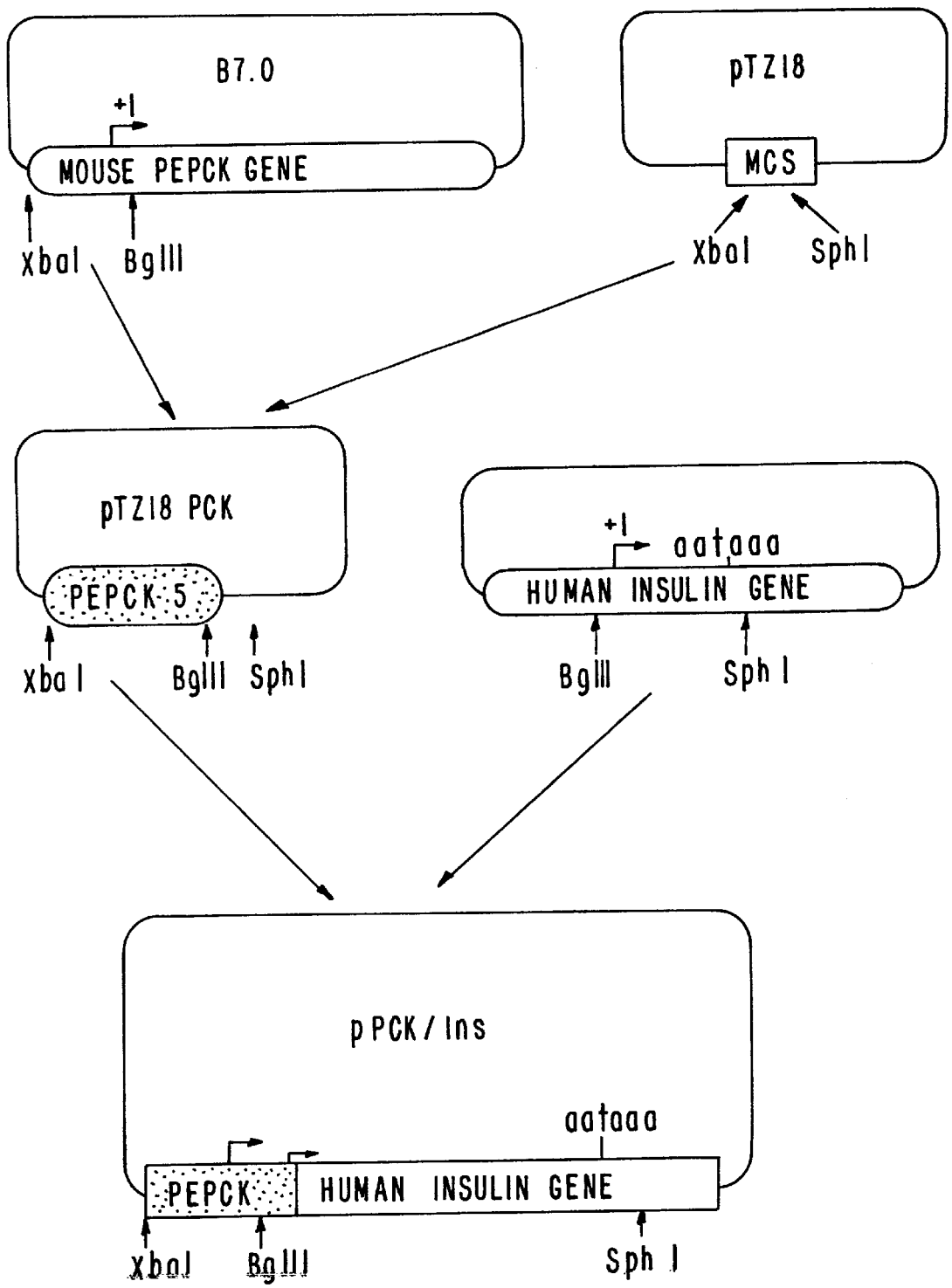
FIG. 1 shows the construction of the PEPCK/insulin chimeric gene from the plasmid pB7.0 and the human insulin gene.

One object of the invention is a chimeric gene using the gene or cDNA (complementary DNA) of insulin driven by a promoter or fusion of promoters, preferably adjustable and activated by the diabetic process.

Preferably, the object of the invention is a chimeric gene which is obtained by fusion of the human insulin gene to the promoter of the P-enolpiruvate carboxyquinase (PEPCK).

P-enolpyruvate carboxyquinase is a key enzyme for the control of the gluconeogenic via, and it is found mainly in the liver, kidney, jejunum and adipose tissue. The activity of this enzyme is regulated as regards the expression of its gene. (Hanson, R. W., et al. (1976) Gluconeogenesis: Its Regulation in mammalian Species. John Wiley & Sons, Inc., New York). The expression of the gene of PEPCK is finely regulated by hormones. Within the fragment of the promoter of PEPCK used (−550 bp to +73 bp) sequences responding to AMPc, glucocorticoids and insulin have been described (Wynshaw-Boris, A. et al. (1984) J. Biol. Chem. 259, 12161–12169; Wynshaw-Boris, A., et al. (1986) J. Chem. 261, 9714–9720; Short, J. M., et al. (1986) J. Biol. Chem. 261, 9721–9726; O'Brien, R. M., et al. (1990) Science 249, 533–537). The glucagon, acting via AMPC, and the glucocorticoids activate the gene expression, while insulin inhibits said expression. The gene expression of the PEPCK is increased in diabetic animals due to the rise in the plasmatic levels of glucagon and the drop in the insulin levels (Tilghman, S. M., et al. (1974) Proc. Natl. Acad. Sci. USA 71, 1304–1308; Hopgood, M. F., et al (1973) Biochem. J. 134, 445–453; Kioussis, D., et al. (1978) J. Biol. Chem. 253, 4327–4332). This fragment of the promoter of PEPCK is able to drive the gene expression of the bovine growth hormone, in a regulated and specific way, of tissue in transgenic animals (NcGrane, MlM., et al. (1988) J. Biol. Chem. 263, 11443–11451; Short, M. K., et al. (1992) Mol. Cell. Biol. 12, 1007–1020; Eisenberger, C. L. (1992) Mol. Cell. Biol. 12, 1396–1403).

Therefore, when fusing to the human insulin gene this promoter of PEPCK insulin will be produced in the tissues where the promoter of PEPCK is expressed. In a diabetic animal the chimeric gene will be transcribed, but when sufficiently sintetized, the insulin itself will inhibit the promoter of PEPCK which drives its expression.

So the object of the invention is the creation of a PEPCK/insulin chimeric gene. In this chimeric gene, the fragment corresponding to the insulin gene keeps 170 bp of the flank zone 5'. The PEPCK/insulin chimeric gene contains two beginnings of transcription, one corresponding to the insulin promoter, and the other one the promoter of PEPCK.

It is actually a chimeric promoter, to which the portion of the promoter of PEPCK confers tissue specificity (mainly liver, kidney, jejunum and adipose). This chimeric gene has been introduced into hepatoma cells in culture and into hepatocytes in primary culture by transitory transfection, the appearance in these cells of insulin specific mRNA in liver and immunoreactive insulin in the culture medium being observed.

Another object of the invention is a method for fusioning promoters or gene regulating elements which allows to express insulin in cell types different from the β-cells of the pancreas. In the chimeric gene, the portion of the promoter of PEPCK confers tissue specificity (mainly liver, kidney, jejunum and adipose).

Also an object of the invention is an expression vector which allows to express insulin in cells different from the β-cells of the pancreas, more particularly, a pPCK/Ins plasmid vector and a vPCK/Ins retroviral vector. These vectors allow the expression of the chimeric gene in cells. Other vectors of viral expression (adenovirus, herpes, virus, papillomavirus, etc.) or non-viral can be used.

They have been used to infect different types of cells in primary culture and established cell lines (hepatoma, fibroblasts, myoblasts, preadipocytes). The infected cell lines express human insulin in a predictable way.

Further, the object of the invention is a transgenic animal expressing the chimeric gene described above, as well as a cell type originated from this transgenic animal.

Transgenic mice have been obtained in the laboratory by means of the technique of microinjection of the chimeric gene into fertilized mouse ovules before the fusion of both the female and male pronuclei. The animals obtained were healthy and normoglycemic, showing that there is a good control in the regulation of the chimeric gene.

Another object of the invention is the chromosome of the transgenic animal containing the above described chimeric gene.

Finally, the object of the invention is a chimeric gene of the above described type, for using in the gene therapy of diabetes, more specifically, for using in the gene therapy of diabetes in tissues different from the pancreas in mammals, particularly, in the human species.

Also, the invention relates to a transgenic animal of the type disclosed for using in the development of gene therapy protocols.

EXAMPLES

For the construction of the PEPCK/insulin chimeric gene (FIG. 1) we started from plasmid pB7.0 which contains the complete gene of PEPCK. By means of digestion with the XbaI and BglII enzymes (fragment from −460 bp to +73 bp), the flank zone 5' of this gene was obtained. This fragment was then subcloned in the polylinker of the pTZ18 plasmid. To this end, this plasmid was driven with XbaI and BglII and the fragment of the promoter was later linked to these target. So the promoted of PEPCK had been subcloned in pTZ18 and there were still some targets in the polylinker that could later be used. Then the human insulin gene was introduced. In this case, the complete gene of insulin was cut with BglII and SphI and the fragment −170 bp to +1561 bp was obtained (Bell, I. B., et al (1980) Nature 284, 26–32). The pTZ18 plasmid, which contained the promoter of PEPCK, was driven with BglII, a target situated at the end of the promoter (end 3'), and SphI, a target situated on the polylinker. This linearized plasmid was linked to the fragment BglII/SphI of the insulin gene, and the PEPCK/insulin chimeric gene was obtained, subcloned in pTZ18 (FIG. 1). This plasmid was named pPCK/Ins.

Figure 2:
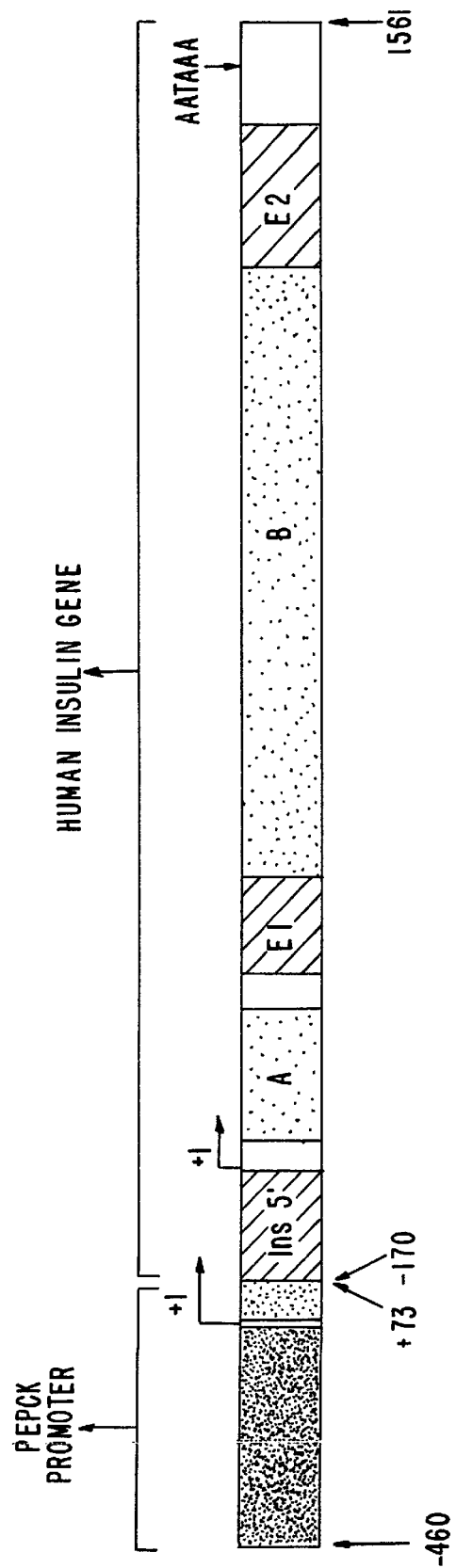
FIG. 2 shows the structure of PEPCK/insulin chimeric gene.

FIG. 2 shows, in detail, the structure of the PEPCK/insulin chimeric gene. The promoter of PEPCK (fragment −460 bp to +73 bp) is fusioned to flank zone 5' of the human insulin gene (−170 bp to +1). This fragment of the promoter of insulin contains the elements recognized by the general machinery of transcription and a *response element to AMPc (which induces the expression of the gene). Therefore, in the flank zone 5' of the chimeric gene were two TATA box and two beginnings of the transcription, one at the end of the promoter of PEPCK and another one at the end of the promoter of insulin. The human insulin gene contains three exons (two codifiers, E1 and E2) and two introns (A and B). In position 5' with respect to the intron A is the cap site and in 3' of the last exon is the polyadenylation signal (FIG. 2).

This chimeric gene has been introduced in hepatoma cells in culture and in hepatocytes in primary culture by transitory transfection of the pPCK/Ins plasmid, the appearance of insulin specific mRNA in these cells and immunoreactive insulin in the culture medium being observed.

Once verified that the PEPCK/insulin chimeric gene was expressed in a predictable way we went over to the obtention of a retroviral vector containing the chimeric gene, and which, in turn, is expressed in a way regulated and controllable by the expression product itself, insulin. This is an essential requirement for producing a vector useful in gene therapy.

Figure 3:
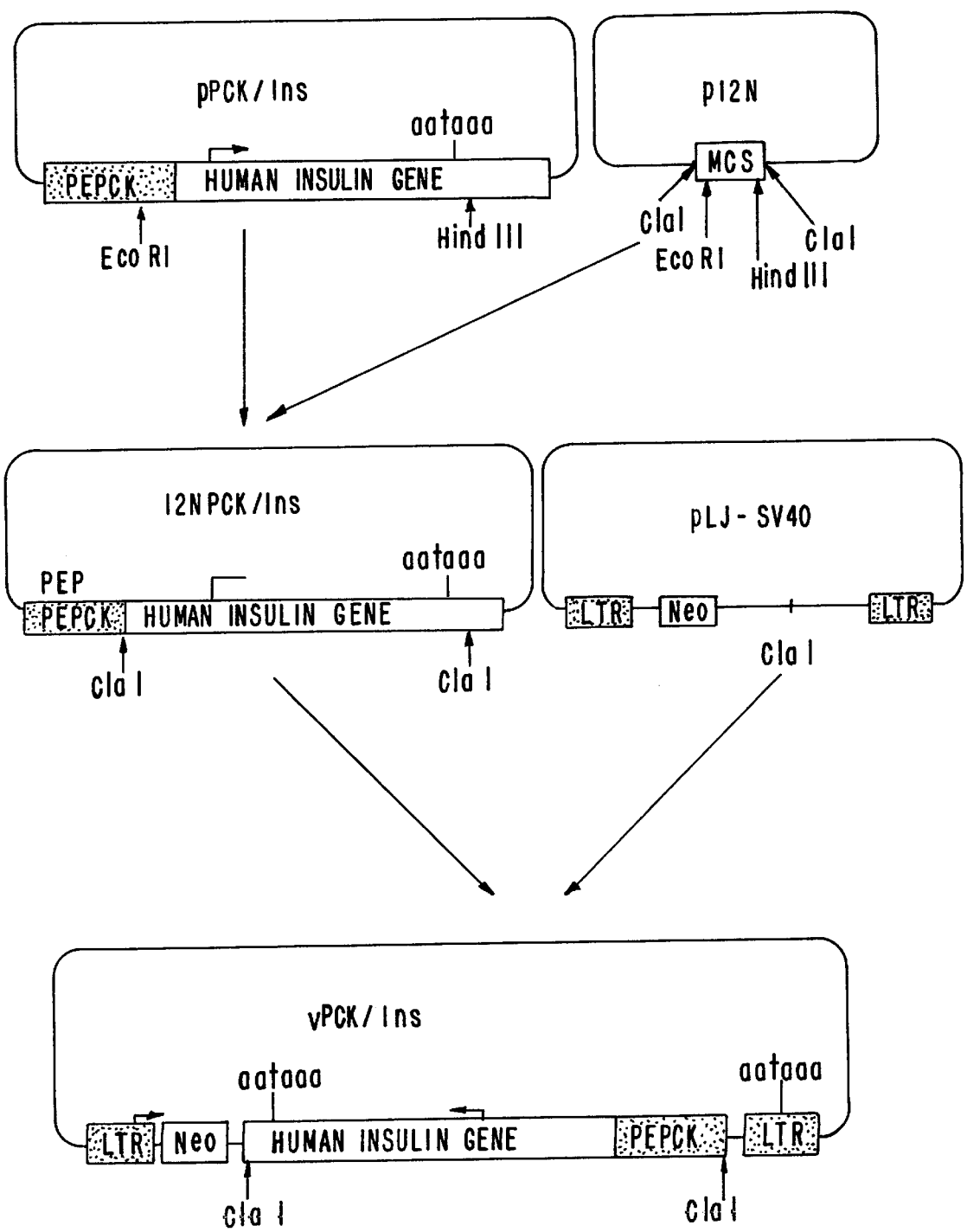
FIG. 3 shows the process for the obtention of the vPCK/Ins retroviral vector from the pPCK/Ins plasmid.

As schematically shown in FIG. 3, the fragment EcoRI-HindIII of the pPCK/Ins plasmid was subcloned for the construction of the retroviral vector, said fragment containing the complete PEPCK/insulin chimeric gene, to the plasmid p12N. The Cla I fragment of the p12NPCK/Ins was then obtained, containing the chimeric gene, and introduced in the Cla I target of the pLJ(-SV40) retroviral vector (derivative from the pLJ parental vector (Korman, A. J., et al. (1987) Proc. Natl. Acad. Sci. USA 84, 2150–2154)). The resulting vector, vPCK/Ins, contains the PEPCK/insulin chimeric gene in an orientation opposite to the LTR 5' (promoter of the retrovirus).

This vector was introduced in psi-2 cells (Mann, R., (1983) Cell 33, 153–159) by precipitation with calcium phosphate. The cells were exposed to the selection antibiotic G418 at 48 hours after transfection, and those which were positive to the integration of the vector survived the toxic. These cells were kept in culture for a month, and when they reached confluence the culture medium was collected, which contained the defective virions.

The process for obtaining a transgenic animal expressing the PEPCK/insulin chimeric gene is briefly described below.

Once verified that the chimeric gene was functional by transfection of culture cells, the chimeric gene was then microinjected (XbaI-SphI fragmento) to mouse fertilized ovules before the fusion of both the female and male pronuclei according to the method described in Wagner, et al. (1981) Proc. Natl. Acad. Sci. USA 78, 5016. These embryos were then transferred to a receptor mother. DNA of the obtained animals was isolated from a tail fragment and then the presence of the transgene was analyzed by Southern blot and further hybridization with a specific probe containing a fragment of the microinjected chimeric gene. With the transgenic animals colonies have been established, in which the expression of the chimeric gene has been analyzed. So the transgenic animals obtained express the transgene in those tissues where PEPCK is ussually expressed. The obtained animals were healthy and normoglycemic, thus showing that there is a good control in the regulation of the chimeric gene.

We claim:

1. A gene construct comprising a PEPCK promoter in operable linkage with a human insulin gene, or the complement of said gene construct.

2. An expression vector comprising the gene construct of claim 1.

3. The expression vector of claim 2 which is the plasmid vector pPCK/Ins.

4. A non-islet host cell transformed by the expression vector of claim 3.

5. The host cell of claim 4 that is selected from the group consisting of a liver cell and a hepatoma cell.

6. The expression vector of claim 2 which is the retroviral vector vPCK/Ins.

7. A non-islet host cell transformed by the expression vector of claim 6.

8. The host cell of claim 7 that is selected from the group consisting of a liver cell and a hepatoma cell.

9. A non-islet host cell transformed by the gene construct of claim 1.

10. The host cell of claim 9 that is selected from the group consisting of a liver cell and a hepatoma cell.

11. The gene construct of claim 1, wherein the PEPCK promoter consists essentially of a PEPCK fragment ranging from −460 bp to +73 bp as defined by FIG. 2.

12. A transgenic mouse whose genome comprises a transgene comprising a PEPCK promoter operably linked to a human insulin gene, wherein expression of said insulin gene in the tissues of said mouse is physiologically regulated such that insulin expression by said gene is downregulated in the presence of physiological concentrations of extracellular insulin resulting in a state of normoglycemia in said mouse.

13. The transgenic mouse of claim 12, wherein insulin expression by said gene is upregulated in the presence of glucagon resulting in a state of normoglycemia in said mouse.

* * * * *